United States Patent [19]

Maxwell, Jr.

[11] 4,013,520
[45] Mar. 22, 1977

[54] PROCESS FOR SEPARATING 2,6-XYLENOL FROM A MIXTURE OF CRESYLIC ACIDS

[76] Inventor: Robert W. Maxwell, Jr., 607 Horizon View Drive, Pittsburgh, Pa. 15235

[22] Filed: May 22, 1975

[21] Appl. No.: 580,056

[52] U.S. Cl. .................................. 203/34; 203/29; 203/38; 260/621 A; 260/627 G
[51] Int. Cl.² ..................... C07C 37/22; B01D 3/14
[58] Field of Search .................. 203/28, 29, 50, 33, 203/34, 38; 260/621 A, 627 G

[56] References Cited

UNITED STATES PATENTS

| | | | |
|---|---|---|---|
| 2,870,192 | 1/1959 | Bonstedt | 260/975 |
| 3,077,491 | 2/1963 | Seglin | 260/975 |

FOREIGN PATENTS OR APPLICATIONS

| | | | |
|---|---|---|---|
| 459,217 | 3/1935 | United Kingdom | 260/966 |
| 1,146,173 | 3/1969 | United Kingdom | |

OTHER PUBLICATIONS

Journal of the Chemical Society, Sec. C., Organic Chem., Part 1, pp. 815–818, London, The Chemical Society, 1968.

Primary Examiner—Hiram H. Bernstein

[57] ABSTRACT

A mixture of cresylic acids containing a substantial amount of 2,6-xylenol is contacted with an ester-forming phosphorus compound in an amount in the range of 0.5 to 5.0 equivalents per equivalent of cresylic acids other than 2,6-xylenol. The temperature is in the range of 50°–250° C., and a catalyst may or may not be employed. Under these conditions, aryl phosphates are formed more rapidly from the cresylic acids other than the 2,6-xylenol. The substantially unreacted 2,6-xylenol is readily separated from the aryl phosphates.

5 Claims, No Drawings

PROCESS FOR SEPARATING 2,6-XYLENOL FROM A MIXTURE OF CRESYLIC ACIDS

BACKGROUND OF THE INVENTION

This invention relates to a process for separating 2,6-xylenol from a mixture of cresylic acids containing 2,6-xylenol; cresol isomers, o-, m-, and p-cresol; and higher homologs.

Cresylic acids are naturally-occurring phenolic compounds found in coal tar distillates derived from low-temperature carbonization of bituminous coal. These compounds also occur in petroleum, in coke oven tars, in oil shale distillates, in coal hydrogenation oils and the like. The 2,6-xylenol appears in certain reaction products as well as in naturally-occurring cresylic acid mixtures. One example is the catalytic methylation of either phenol or o-cresol which provides mixtures containing 2,6-xylenol. The 2,6-xylenol (2,6-dimethylphenol) is a valuable material for use in antioxidants, plasticizers and the like. It also may be useful as a monomer in the preparation of polymers.

The problem of separating 2,6-xylenol in good yield and high purity from cresylic acids in difficult because the cresol isomers have boiling points that are similar to the boiling point of 2,6-xylenol. According to Bulletin 606, Bureau of Mines, "Properties of Compounds in Coal-Carbonization Products" by H. C. Anderson and W. R. K. Wu, the following cresylic acids at a pressure of 760 mm of mercury have the following boiling points:

| | | |
|---|---|---|
| 2,6-xylenol | - | 201° C. |
| o-cresol | - | 191.003° C. |
| m-cresol | - | 202.231° C. |
| p-cresol | - | 201.940° C. |

In view of the relatively close boiling points of these cresylic acids, the prior art has resorted to both physical and chemical methods for separating such mixtures. Successive fractional distillation, fractional azeotropic distillation, double solvent extraction, azeotropic distillation with a non-polar branched alkene and other methods have been suggested. The separation by the process of this invention is simpler and more economical than the prior art processes. The process involves formation of arylphosphates, especially triarylphosphates, primarily from the cresylic acids.

The preparation of alkylated triaryl phosphates have been known for many years. The classical method of forming triarylphosphates is by the reaction of alkyl phenol with phosphorus oxychloride. In British Pat. No. 1,146,173 by Wilfred Pickles and Donald Richard Randall entitled, "Production of Triaryl Phosphate," a method of triarylphosphate production using a catalyst is disclosed. This patent also discloses in its comparative examples that phosphorylation of commercially available cresols produces an inferior phosphate ester than the alkylated phenols of its process. The commercially available cresol contained around 1.5% 2,6-xylenol along with o-cresol, 2,4-xylenol, 2,3-xylenol, 2,5-xylenol, 3,4-xylenol, 3,5-xylenol and predominantly p-cresol and m-cresol. This disclosure shows that triarylphosphates can be formed from the above compounds.

An article entitled, "Structural Effects in Reactions of Organophosphorus Compounds. I. Reactions of Phosphorus Oxychloride with Hindered Phenols," discusses the reaction of phosphorus oxychloride (POCl) with 2,6-dialkyl-phenols to form triaryl phosphates. The conclusion of the article is that 2,6-dialkyl phenols exhibit little steric hindrance on reaction with $POCl_3$ unless the alkyl substituent is bulky like a t-butyl alkyl substituent. Where these bulky substituents are present, reaction with $POCl_3$ occurs only in the presence of Friedel-Crafts type catalysts after either a dealkylation or a rearrangement has occurred. With smaller alkyl substituents the phenols show a relatively slower rate of reaction with phosphoryl chloride. In this article, 2,6-xylenol was reacted directly with $POCl_3$ and other phosphorochloride compounds with and without a catalyst. Several reactions were completed while other reactions did not start. When an equimolar amount of catalyst was used, the reaction went to completion and formed 2,6-dimethylphenylphosphorodichloridate.

It is an object of this invention to provide a process for separating 2,6-xylenol from a mixture of cresylic acids which will permit recovery of the 2,6-xylenol in good yields at a high purity.

SUMMARY OF THE INVENTION

The process of this invention is based on the 2,6-xylenol being less reactive than other cresylic acids in the formation of aryl phosphate esters. Accordingly, the process comprises contacting a mixture of cresylic acids with an ester-forming phosphorus compound to produce a second mixture containing aryl phosphate esters formed primarily from cresylic acids other than 2,6-xylenol, and unreacted 2,6-xylenol and separating the aryl phosphate esters from the unreacted 2,6-xylenol.

The mixture of cresylic acids, which includes 2,6-xylenol and cresol isomers and other higher homologs, is contacted with an amount of ester-forming phosphorus compound in the range of 0.5 to 5.0 equivalents per equivalent of other cresylic acids at a temperature in the range of 50°–250° C. in the presence or absence of a catalyst. Under these conditions the cresylic acids other than 2,6-xylenol form aryl phosphate esters more rapidly than the 2,6-xylenol. Hence, the other cresylic acids are esterified to form the aryl phosphate ester while leaving the less reactive 2,6-xylenol substantially unreacted. The aryl phosphate esters have boiling points substantially higher than the boiling point of 2,6-xylenol. The 2,6-xylenol can be easily separated from the aryl phosphate esters by distillation.

When a catalyst is used in the treating step any Lewis acid, Bronsted acid, hydrogen acid, Friedel-Crafts, catalyst, or anhydrous condensation catalyst may be used.

The terms used in the description of the process of this invention are clarified by the following definitions: The term "cresylic acids" includes a mixture of the various cresol isomers and higher homologs and xylenols, including 2,6-xylenol. The term "ester-forming phosphorus compound" includes phosphorus oxyhalides, phosphorus trihalides, phosphorus pentahalides and phosphorus thiohalides. The term "other cresylic acids" includes cresylic acids other than 2,6-xylenol.

DETAILED DESCRIPTION OF THE INVENTION

It is believed, without limiting the process of this invention, that the 2,6-xylenol is less reactive than the other cresylic acids in reaction with an ester-forming phosphorus compound because of steric hindrance. The reaction with the ester-forming compound occurs at the oxygen in a phenolic compound. The methyl groups in the 2-position and 6-position in juxtaposition to the oxygen at the 1-position on the aromatic ring interfere with the ability of the ester-forming phosphorus compound to reach the oxygen.

In the preferred embodiment of this invention the 2,6-xylenol is purified from a mixture where the other cresylic acids are impurities and where the 2,6-xylenol is the major component of the mixture. However, the process of this invention may be used to separate any quantity of 2,6-xylenol from any quantity of cresylic acids. Also, in the preferred embodiment, it is desired to obtain the maximum purity of 2,6-xylenol. The maximum purity is obtained by employing a catalyst. Maximum purity of 2,6-xylenol cannot be reached when a catalyst is not employed in the esterification. The purity reached in the absence of a catalyst is less than maximum purity because the aryl phosphates formed by esterification are partially degraded to new cresylic acid isomers. The partial degradation occurs on account of the more extreme condition of temperature and reaction time needed to accomplish esterification in the absence of a catalyst.

A mixture containing 2,6-xylenol and cresylic acid impurities is contacted with an ester-forming phosphorus compound which esterifies the cresylic acid impurities and a small amount of 2,6-xylenol. This contacting is at a temperature in the range of 50°–250° C. The quantity of ester-forming phosphorus compound used in the esterification is preferably 2 equivalents to 1 equivalent of the cresylic acid impurities. This assures the reaction of all the cresylic acid impurities to form aryl phosphates. The aryl phosphates formed by this contacting are predominantly triarylphosphates but a small amount of diarylphosphates on the order of less than 5% may also be formed.

The aryl phosphates have a higher boiling point than the 2,6-xylenol and the two can be easily separated by distillation. The 2,6-xylenol distills at a temperature of 82°–201° C. at a pressure of 10–760 mm of mercury and preferably 118°–135° C. at a pressure of 50–100 mm of mercury. The aryl phosphates distill at a temperature of 200°–400+° C. at a pressure of 1–750 mm of mercury and preferably at a temperature of 215°–240° C. at a pressure of 3–5 mm of mercury. These distillation conditions are preferred but any other distillation conditions known to those skilled in the art may be used.

The catalyst used in contacting the ester-forming phosphorus compound and the mixture of 2,6-xylenol and other cresylic acids may be selected from an anhydrous condensation catalyst, a Friedal-Crafts catalyst, a Lowry or Bronsted acid catalyst or a hydrogen acid catalyst. Suitable catalysts include, but are not limited to, the chlorides of Al, Fe, Cr, Ti, Sn, Zn, Mg, or Ca. The preferred catalyst is aluminum chloride. The quantity of $AlCl_3$ catalyst used is in the range of 0.05–5.0% of unpurified 2,6-xylenol and preferably 0.5–1.0%.

Ester-forming compounds are those phosphorus compounds which will yield organic phosphates or phosphites when reacted with alcohols. The preferred ester-forming phosphorus compound used to contact the mixture of 2,6-xylenol and cresylic acid impurities is phosphorus oxychloride. It is to be understood that substantially similar results may be obtained when other phosphorus oxyhalides or halides or thiohalides are employed, e.g., phosphorus oxybromide, phosphorus oxybromide dichloride ($POBrCl_2$), phosphorus oxydibromide chloride ($POClBr_2$), phosphorus thiochloride ($PSCl_2$), phosphorus thiobromide ($PSBr_3$), phosphorus thiobromodichloride ($PSBrCl_2$), phosphorus trihalides, e.g., phosphorus trichloride or tribromide, phosphorus pentahalides, e.g., phosphorus pentachloride or phosphorus pentabromide.

The process of this invention may be performed in a batch or continuous operation. The continuous operation can be accomplished by providing two reaction vessels and cascading the reactants from one to the other with a predetermined holding time in each vessel. The one vessel is for the contacting step and the other vessel is for the distillation step. Also, the continuous operation can be accomplished by using one vessel that has two different stages.

For a better understanding of the invention, reference should be had to the following description of four experimental runs conducted on a mixture containing 2,6-xylenol, and ortho-cresol, meta-cresol and para-cresol, the cresol isomers.

EXAMPLE I

In this example a 92% 2,6-xylenol solution was upgraded to a 96.7% purity. A mixture containing 524 grams of 92% 2,6-xylenol, 7% meta-, and paracresols and 1% ortho-cresol was charged into a 1-liter flask. Anhydrous $AlCl_3$ (2.5 grams) was added to the flask in order to catalyze the selective esterification. Next, 27.5 grams (0.54 equivalents) of $POCl_3$ was added to the mixture to esterify selectively the 0.43 equivalents of cresols present in the mixture. The reaction temperature was gradually raised from 50° C. to 185° C. in seven hours and held at 185° C. until the $POCl_3$ was completely reacted. The complete reaction of $POCl_3$ took two hours and yielded a crude product. This crude product was distilled to produce a purified product. Gas chromatographic analysis of the purified product indicated 96.7% of 2,6-xylenol, 1.8% orthocresol and 1.6% meta-, and para-cresols.

EXAMPLE II

In this example a 90% 2,6-xylenol solution was upgraded to a 99.8% purity. A mixture containing 524 grams of 90% 2,6-xylenol and 8% meta-, and para-cresols and 2% ortho-cresol was charged into a 1-liter flask. Anhydrous $AlCl_3$ (2.6 grams) was added to the mixture in order to catalyze the selective esterification. Next, 51.0 grams (1.0 equivalents) of $POCl_3$ was added to the mixture of esterify selectively the 0.47 equivalents of cresols present in the mixture. The temperature was gradually raised from 55° C. to 180° C. over a period of 4.5 hours and the temperature was held at 180° C. until the $POCl_3$ was completely reacted. This took a period of time of 1.0 hour and yielded a product containing 2,6-xylenol and phosphate esters of the cresols present.

This product was vacuum distilled to obtain 400 grams of 99.8% 2,6-xylenol distilling at 118°–119° C. at a pressure of 50 mm of Hg. and 109 grams of phosphate ester distilling at 215°–230° C. at a pressure of 3mm of mercury.

EXAMPLE III

In this example a 91% 2,6-xylenol solution was upgraded to 99% purity. A mixture containing 530 grams of 91% 2,6-xylenol and 8% meta-, and para-cresols and 1% ortho-cresol was charged into a 1-liter flask. Anhydrous $AlCl_3$ (2.6 grams) was added to the mixture to catalyze the selective esterification. Next, 50 grams (0.98 equivalents) of $POCl_3$ was added to the mixture to esterify selectively the 0.47 equivalents of cresols present. The reaction temperature was gradually raised from 54° C. to 185° C. over a period of time of 4.5 hours. The temperature was held at 185° C. until the $POCl_3$ was completely reacted, which took a period of time of 1.5 hours. A crude product was obtained.

The crude product was neutralized with lime and then vacuum distilled to obtain 401 grams of 99.8% 2,6-xylenol distilling at 134°–135° C. at a pressure of 100 mm of mercury.

EXAMPLE IV

In this example the purification of 2,6-xylenol from a mixture containing 2,6-xylenol, ortho-, meta-, and para-cresols by selective esterification of the cresols with $POCl_3$ was conducted without the use of a catalyst.

A mixture containing 528 grams of 91% 2,6-xylenol and 8% meta-, and para-cresols and 1% ortho-cresol was charged into a 1-liter flask. The temperature was adjusted to 50° C. and 50 grams (0.98 equivalents) of $POCl_3$ was added to the mixture to esterify selectively the 0.46 equivalents of cresols present. The reaction temperature was gradually raised from 54° C. to 190° C. over a four hour period of time. Gas chromatographic analysis of a sample of the mixture after this four hour period showed the mixture contained 95% 2,6-xylenol, 1% ortho-cresol and 4% meta-, and para-cresol.

After the gradual increase in temperature, the mixture was refluxed at a temperature of 190°–195° C. for four hours. After reflux, the mixture had a 2,6-xylenol purity of 96% according to gas chromatographic analysis.

However, after 6 hours of additional reflux at 195° C., the 2,6-xylenol purity actually dropped to 93%. Gas chromatographic analysis at this point showed the formation of two new cresylic acid isomers. This indicated the phosphate ester of the cresol impurities had been partially degraded under these conditions.

These results emphasize the importance of using a catalyst to obtain 2,6-xylenol with a purity of 99.8% through selective esterification of the cresol impurities with $POCl_3$.

According to the provisions of the patent statutes, the principle, preferred construction and mode of operation have been explained and what is considered to represent its best embodiment has been illustrated and described. However, it should be understood that within the scope of the appended claims, the invention may be practiced otherwise than as specifically illustrated and described.

I claim:

1. A process for purifying 2,6-xylenol from a mixture containing cresylic acids wherein 2,6-xylenol is present as a major component in the mixture and the cresylic acids other than 2,6-xylenol are present as impurities, comprising:

contacting the mixture containing 2,6-xylenol and cresylic acid impurities with an ester-forming phosphorus compound in an amount in the range of 0.5 to 5.0 equivalents per equivalent of cresylic acids other than 2,6-xylenol and at a temperature in the range of 50°–250° C to produce a second mixture containing aryl phosphate esters, formed primarily from the cresylic acids other than 2,6-xylenol, and unreacted 2,6-xylenol; and distilling the unreacted 2,6-xylenol from the aryl phosphate esters and in the second mixture.

2. A process according to claim 1 wherein the ester-forming phosphorus compound is selected from the group consisting of phosphorus oxyhalides and phosphorus halides and phosphorus thiohalides.

3. A process for purifying 2,6-xylenol from a mixture containing cresylic acids wherein 2,6-xylenol is present as a major component in the mixture and the cresylic acids other than 2,6-xylenol are present as impurities, comprising:

contacting the mixture containing 2,6-xylenol and cresylic acid impurities with an ester-forming phosphorous compound in an amount in the range of 0.5 to 5.0 equivalents per equivalent of cresylic acids other than 2,6-xylenol and at a temperature in the range of 50°–250° C and in the presence of a catalyst selected from the group consisting of Friedel-Crafts catalyst, anhydrous condensation catalyst, Lewis acids, Bronsted acids, and hydrogen acids to produce a second mixture containing aryl phosphate esters, formed primarily from the cresylic acids other than 2,6-xylenol, and unreacted 2,6-xylenol; and distilling the unreacted 2,6-xylenol from the aryl phosphate esters in the second mixture.

4. A process according to claim 3 wherein the catalyst is aluminum chloride present in an amount in the range of 0.05% to 5.0% based on the amount of 2,6-xylenol present in the mixture.

5. A process according to claim 3 wherein the ester-forming compound is selected from the group consisting of phosphorus oxyhalides and phosphorus halides and phosphorus thiohalides.

* * * * *

UNITED STATES PATENT OFFICE
CERTIFICATE OF CORRECTION

PATENT NO. : 4,013,520
DATED : March 22, 1977
INVENTOR(S) : Robert W. Maxwell, Jr.

It is certified that error appears in the above-identified patent and that said Letters Patent are hereby corrected as shown below:

| | |
|---|---|
| Col. 1, line 24 | After "acids" the word 'in' should be --is--. |
| Col. 4, line 56 | After "mixture" the word 'of' should be --to--. |
| Col. 6, line 21 | After "esters" the word 'and' should be deleted. |

Signed and Sealed this twenty-sixth Day of July 1977

[SEAL]

Attest:

RUTH C. MASON
*Attesting Officer*

C. MARSHALL DANN
*Commissioner of Patents and Trademarks*